United States Patent [19]

Yukl

[11] Patent Number: 4,947,848
[45] Date of Patent: Aug. 14, 1990

[54] DIELECTRIC-CONSTANT CHANGE MONITORING

[75] Inventor: Tex Yukl, Baker, Oreg.

[73] Assignee: Spatial Dynamics, Ltd., Baker, Oreg.

[21] Appl. No.: 693,388

[22] Filed: Jan. 22, 1985

[51] Int. Cl.$^5$ .................................................. A61B 5/05
[52] U.S. Cl. ................................ 128/653 R; 128/645;
                                           128/736; 324/71.1
[58] Field of Search ............... 128/645, 646, 647, 653,
                    128/670, 672, 694, 1.4; 324/71.1, 452, 228

[56] References Cited

U.S. PATENT DOCUMENTS 4,079,730  3/1978  Wikswo, Jr. et al. ............... 128/653
4,234,844  11/1980  Yukl .
4,318,108  3/1982  Yukl .

*Primary Examiner*—Ruth Smith
*Attorney, Agent, or Firm*—Kolisch, Hartwell & Dickinson

[57] ABSTRACT

A method for monitoring, over time, changes that occur in the apparent dielectric constant of a selected volumertic space. The selected space may be formed by a substantially homogenous material, in which case, dielectric-constant changes are interpretable, according to the invention, to indicate pressure and/or temperature changes in the space. In another situation, the selected space may be nonhomogenous, in which case dielectric-constant changes are interpretable, also according to the invention, to indicate relative volumetric changes between different media within the space.

4 Claims, 1 Drawing Sheet

U.S. Patent  Aug. 14, 1990  4,947,848
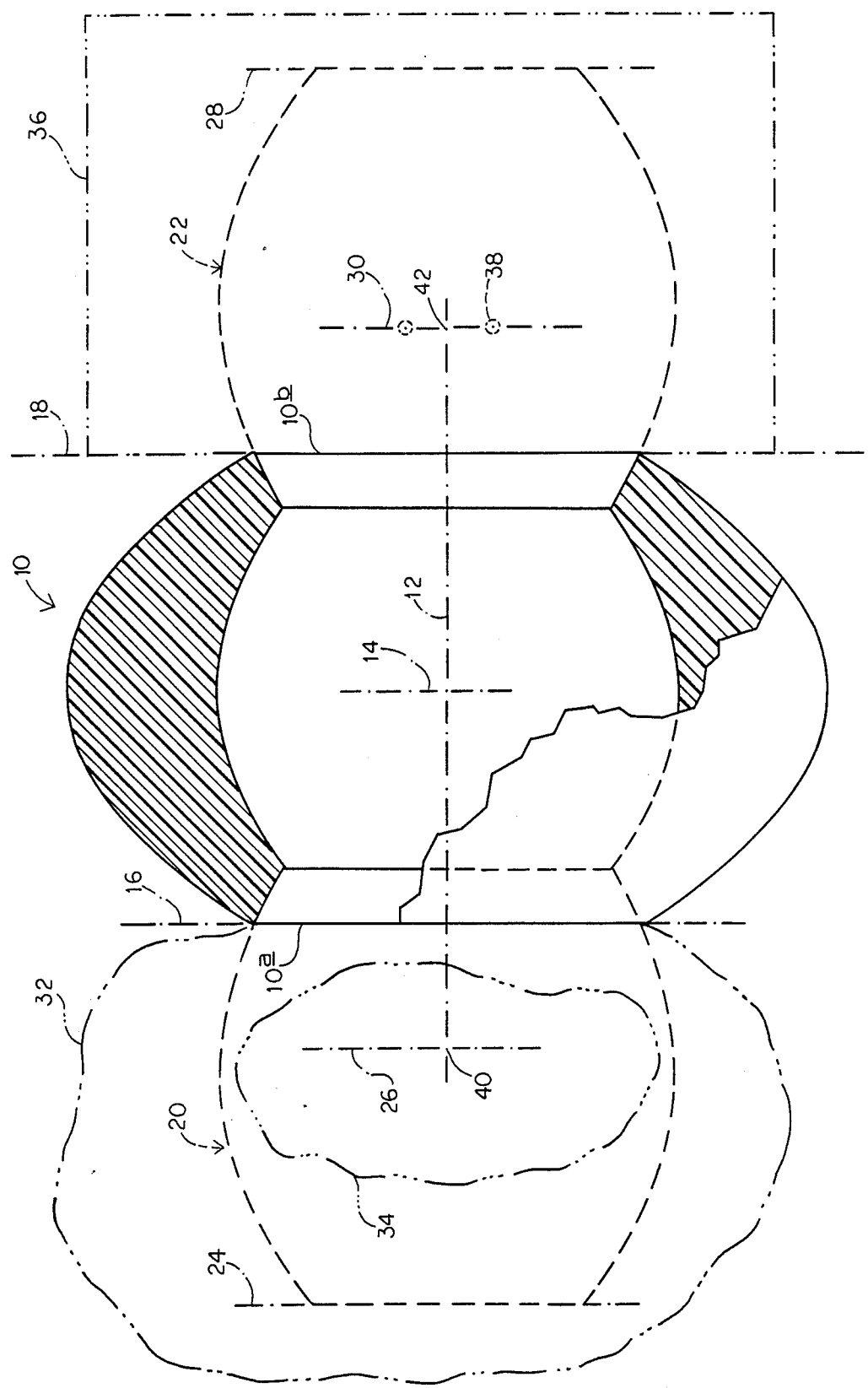

DIELECTRIC-CONSTANT CHANGE MONITORING

BACKGROUND AND SUMMARY OF THE INVENTION

The present invention relates to a diagnostic method for monitoring time-based changes in the apparent nominal dielectric constant which characterizes a defined space, all for the purpose of interpreting these changes as direct indications of other kinds of changes (i.e., pressure changes, temperature changes and relative volumetric changes) occurring within the space. For the purpose of illustration herein, preferred methods of practicing the invention are described in conjunction, on the one hand, with monitoring heart activity within a person's chest, and on another hand, with monitoring pressure changes which occur within the human eyeball (for example, to monitor and diagnose a glaucoma situation).

The technology of the present invention is related to subjects disclosed in two prior patents of mine—one of these being U.S. Pat. No. 4,234,844, issued Nov. 18, 1980 for "ELECTROMAGNETIC NONCONTACTING MEASURING APPARATUS", and the other being U.S. Pat. No. 4,318,108, issued Mar. 2, 1982 for "BI-DIRECTIONALLY FOCUSING ANTENNA". The first-mentioned of these two patents discloses a technique employing a bi-directionally radiating, special, doughnut-shaped antenna to monitor electrical activity at one of the two focal points for the antenna as an indication of various phenomena occurring at that focal point. The second-mentioned of the two patents describes, in detail, the construction and special operating features of the antenna utilized in the disclosure of the first-mentioned patent. The disclosures of both patents are incorporated herein by reference.

The present invention is related to yet a new method for employing an antenna like that disclosed in these two prior patents. It is based on special sizing of the antenna, and on a cooperating, adjacent body exhibiting a known nominal dielectric constant, to take advantage of certain volumetric radiation characteristics existing on opposite sides of the antenna, for the purpose of viewing a defined space to observe therein time-based changes in the apparent nominal dielectric constant in the space.

An important object of the invention, pursuant to the statements just made above, is to provide a unique method which enables extremely accurate measuring of the type indicated in a speedy, harmless, noninvasive and nondestructive way.

A related object is to provide such a method which is readily adaptable to an extremely wide variety of measurement environments.

Two procedures are described hereinbelow, for illustration purposes, generally in the field of medicine, wherein the method of the invention has been found to offer particular utility.

DESCRIPTION OF THE DRAWING

The single drawing FIGURE is a simplified side (partially sectional) schematic diagram illustrating apparatus employed in the practice of this invention, and two important applications of the method of the invention.

DETAILED DESCRIPTION OF THE PREFERRED MANNERS OF PRACTICING THE INVENTION

With reference to the drawing, indicated generally at 10 is a bi-directionally radiating antenna which is constructed in accordance with the teachings of the two patents referred to above, and which is sized for use in the practice of the invention according to the teachings given below. Antenna 10, which is somewhat doughnut-shaped, is shown with its near wall in the FIGURE partially fragmented to reveal its inside shape. Certain internal structure has been omitted in order to simplify the drawing.

Antenna 10 has a radiation axis 12, and a central radiation plane (normal to the plane of the drawing) shown at 14. What might be thought of as the two radiation exit faces of the antenna are shown at 10a, 10b, with these faces lying substantially in planes 16, 18, respectively, which planes are parallel to and equidistant from plane 14.

As will become apparent, the particular sizing which is decided upon for antenna 10, in order to enable it to perform properly in accordance with the invention, will depend upon what is referred to herein as the apparent nominal dielectric constant of the particular space in which measurement activity is to take place. A reason for this is that the propagation velocity and wavelength of radiated electromagnetic energy are dependent upon the nominal dielectric constant of the space wherein such radiation exists. Subject matter, still to be described, which is illustrated adjacent the antenna's exit faces, on the left and right sides of the drawing, depend for proper proportion on the particular nominal dielectric constant involved, and because of this, and further because of the fact that the single drawing FIGURE is used to illustrate two different measurement procedures, no effort has been made to proportion these illustrations exactly with respect to one another, or with respect to the illustrated geometry of the antenna. The description presented below, however, precisely mathematically defines the proper proportions.

When antenna 10 is energized, it radiates energy bi-directionally along axis 12 to create generally symmetrically organized radiation fields adjacent opposite exit faces of the antenna. Illustrated (in an idealized sense) in dashed outline at 20 (adjacent exit face 10a), and in dashed outline at 22 (adjacent exit face 10b), are portions of these radiation fields, which are referred to herein as defined-power-characteristic radiation volumes. Generally speaking, these defined volumes may be thought of as volumes of revolution which are symmetric with respect to axis 12, with the volumes, if antenna 10 is radiating on its opposite sides into media having like nominal dielectric constants, being substantially mirror images of one another. In a sense, each of these two defined volumes may be thought of as having the shape of an end-truncated football (truncated, substantially ellipsoidal shape).

In the drawing, the right boundary of volume 20 is defined by plane 16, and the left boundary by a plane 24. Extending between these two planar boundaries is a curvilinear, shell-like boundary whose intersections with the plane of the drawing are evident. The curvilinearity of this boundary is formed by cosine curvature similar to that which defines the inside shape of antenna 10 (see the two referenced prior patents). The antenna, once its desired operating frequency has been chosen (as will be explained below) is designed as if it were always to function in air, which has a dielectric constant, $K_a$, of one. Hence, its "cosine curvature," vis-a-vis amplitude, is designed with this dielectric constant in mind. The radiation volumes, typically, will exist in media characterized by a nominal apparent dielectric constant which is greater than unity, and this situation will result in their "cosine curvatures" differing in amplitude in a manner directly relating to the difference between unity and the media's nominal apparent dielectric constants. Frequency, of course, is the same for both the antenna and the media.

The curvilinear boundary of volume 20, and the left planar boundary 24, define what may be thought of as the 3-db power boundaries for the volume. Put another way, energy radiated to these boundaries has, at roughly the locations of the boundaries, one-half the power existing at points 40, 42, the created foci of antenna 10.

Further referring to defined volume 20, the maximum diameter of the volume, relative to axis 12, occurs substantially in a plane 26 which resides, relative to exit face 10a, substantially a distance of one-eighth of the wavelength of radiated energy in the volume. The exact mechanical distance of plane 26 from plane 16, of course, depends upon the dielectric constant which is nominal to the material occupying volume 20. The volume's diameter in plane 26 is substantially one-half the radiation wavelength, and the distance between plane 26 and plane 24 is substantially one-quarter the radiation wavelength.

Because of design considerations which have been taken into account (in a manner which will be expressed shortly), antenna 10 is depicted in the FIGURE in a condition wherein the spatial regions adjacent its opposite faces have substantially the same nominal apparent dielectric constants and loss tangents. Accordingly, radiation volume 22 adjacent exit face 10b is, in fact, shown to be the mirror image of volume 20. The left boundary of volume 22 is defined by plane 18, and the right boundary in the FIGURE by a plane 28. The maximum diameter of volume 22 occurs in a plane 30 which lies the same distance from plane 14 as does previously mentioned plane 26.

Directing attention again to the left side of the drawing, two forms, 32, 34, are shown by dash-double-dot and dash-triple-dot lines, respectively. For the purpose of illustrating one manner of practicing the invention, which will be the first one to be described below, form 32 represents a fragmentary portion of the human chest cavity, with form 34 representing the heart within that cavity. For the purpose of illustrating another manner of practicing the invention, form 32 represents a portion of a human eyeball, and form 34 is ignored entirely.

Let us begin with an illustration of the invention wherein the measuring or monitoring which is to take place involves observing the time-based pumping activity of the human heart illustrated in the FIGURE by form 34. The heart, during pumping, expands and contracts (changes volume), and it is this specific activity, and its effect upon apparent dielectric constant, to which the first procedure of the invention now to be described will look. To begin with, it should be understood that the particular spatial region which is examined according to the invention is defined by one of the defined radiation volumes, and in the case illustrated in the drawing, by volume 20. Accordingly, and in the matter of monitoring heart-pumping activity, where the heart is known to have generally one dielectric constant while residing in a chest cavity that has a different dielectric constant, it is important that volume 20 be designed so that it will completely encompass the volume of the heart when the heart is in its maximum-volume condition. From widespread knowledge about the size and location of the human heart in a given size individual, it is a relatively easy matter to assure that this condition is met.

In the drawing FIGURE, form 34 representing the heart is shown with an oblong upright disposition, typical of the human heart, and in particular, is depicted with a total overall height which represents the largest dimension that the heart achieves in its maximum-volume condition during pumping. This dimension will be some relatively well-known dimension, and for the purpose of further explanation, let us assign it the value X. Knowing that this dimension is to be completely contained within volume 20, and knowing that it is possible to design the antenna in such a manner that the heart will substantially occupy plane 26 (the maximum diameter plane of volume 20), one knows that X must be less than the maximum diameter of the volume, which was expressed earlier as being one-half the operating wavelength in the space embraced by volume 20. Obviously, in a situation such as the one now being described, the space embraced by volume 20 is a nonhomogeneous space, and, in fact, is occupied by substances that have quite different dielectric constants. Accordingly, it is necessary to determine what is referred to herein as the nominal apparent dielectric constant, $K_{na}$, for this space. This has been accomplished with extremely satisfactory results by working from medical information which, by percentage, tells one the respective portions of a person's entire chest cavity occupied by materials having different known dielectric constants. From this information, $K_{na}$ the chest cavity as a whole is readily calculated, and experience has shown that successful practice of the invention can rely on the assumption that the nominal apparent dielectric constant within the space embraced by volume 20 may be assumed to be the same value.

Accordingly, design considerations begin with determining that the known value X must be less than $0.5\lambda K_{na}$, where $\lambda K_{na}$ is the wavelength of radiation produced in accordance with the determined value for $K_{na}$. Equation (1) presented immediately below sets up a condition where X is indeed less than $0.5\lambda K_{na}$, and has been found to produce a very workable design.

$$X = 0.45 \lambda K_{na} \qquad (1)$$

With dimension X known, for example in inches, equation (2) provides a solution for the value of $\lambda K_{na}$ in inches:

$$\lambda_{Kna} = \frac{X}{0.45} \qquad (2)$$

With $\lambda K_{na}$ now known in inches, the operating frequency of the antenna is calculated in accordance with the following well-known equation:

$$f = \frac{11811.024}{\lambda_{Kna} \sqrt{K_{na}}} \qquad (3)$$

Equation (3) yields operating frequency in megahertz.

With the operating frequency of the antenna now known, and employing the teachings expressed in the two earlier-referred-to U.S. patents, the precise design of antenna 10 is determined. More specifically, knowing now what the required operating frequency must be, the antenna is designed as if it were going to operate purely in air where the dielectric constant is unity. Thus, the wavelength (in inches) in air for the just-determined operating frequency is calculated in accordance with equation (4):

$$\lambda_a = \frac{11811.024}{f} \ (K \text{ factor } (.701)) \qquad (4)$$

With this wavelength calculated, the remaining antenna design activities take place in accordance with the teachings of the '844 and '108 patents.

Completing now a description of what is shown in the drawing, from the calculations previously performed which define the exact sizes and shapes of volumes 20, 22, a block of material, shown in dash-double-dot lines at 36, is prepared for placement adjacent exit face 10b with a size which will completely encompass volume 22, and with a dielectric constant which is substantially equal to $K_{na}$. Suitably embedded within this material, at the location of and lying within plane 30, is a conductive receiving ring 38. Ring 38, for maximum signal reception, preferably has a nominal circumference which equals $\lambda K_{na}$.

Explaining now the monitoring method of the invention with respect to observing heart activity as indicated by heart volume changes over time, antenna 10 is placed with its exit face 10a disposed against a patient's chest wall, with axis 12 substantially centered on the predicted location of the heart. Block 36 is suitably placed substantially as shown adjacent exit face 10b. With the antenna energized, voltage and current conditions are monitored in ring 38, and changes in these conditions which occur over time directly proportionately follow simultaneous changes taking place in the volume of the heart. The principal reason for this is that as the heart's volume increases and decreases, the heart occupies greater and lesser amounts of the total space within volume 20, and thus tends to shift proportionally the apparent nominal dielectric constant of the material encompassed by volume 20, and hence, its effect upon antenna 10.

Experience has shown that by careful sizing of antenna 10 to produce defined volumes 20, 22 which are capable of embracing a volume-changeable unit, such as the heart, extremely accurate time-based, volume-change measurements can be made. Accordingly, an in the case of employing the invention to monitor heart activity, a great deal of accurate information can be obtained about heart functioning in a noninvasive, nondestructive, speedy manner. A typical operating power level for antenna 10 in a heart-monitoring operation is about 0.8 micro-watts per cm² at points 40, 42. Careful comparison of the phase, amplitude and polarity effect of the received signal to known references can result in capturing data only available through high risk catheterization procedures presently performed in carefully monitored hospital environments.

The specific operation just described is obviously one which takes place in a circumstance where the defined energy volume produced by the antenna encompasses a volume-changing element having one dielectric constant which is located in a surrounding medium having another dielectric constant. Another type of important operating setting for the invention is one in which the antenna is designed to create a defined energy volume that is intended to be placeable within the boundaries of a body, wherein dielectric constant is substantially uniform throughout the entirety of the space embraced by the energy volume. For example, an important operating field for the invention is in the examination of the human eye for time-based pressure changes which may indicate a glaucoma condition. Pressure changes within the eyeball which come about as a consequence of a glaucoma condition produce time-based changes in the apparent nominal dielectric constant of the eye, and because of these, are uniquely suited for accurate monitoring by the method of the invention.

Considerations about how an antenna, like antenna 10, may be designed to produce energy volumes, like volumes 20, 22, especially suited to such a condition are now set forth.

Let us now assume that form 32 on the left side of the drawing FIGURE represents a fragmentary portion of a human eyeball. Medical and scientific studies indicate that the human eyeball substantially represents a material having what might be thought of as dielectric-constant homogeneity. Accordingly, the antenna is designed to be able to produce an energy volume which can easily be place substantially completely within the confines of the eyeball so as to assure that it embraces a space characterized by substantially uniform dielectric constant. Since the usual dimensions of the eyeball are known, it is an extremely simple matter, employing an equation somewhat like equation (1) above, to determine an appropriate value for $\lambda K_{na}$. If, for example, the maximum diameter of the eyeball is given the value X, and one knows that an energy volume produced by the antenna, like volume 20, must reside within dimension X, one might begin by using an equation, such as equation (5):

$$X = 0.55 \ \lambda K_{na} \qquad (5)$$

This will assure that the maximum dimensions of the produced energy volume will readily fit within the confines of the eyeball, and referring to the left side of the drawing FIGURE, it will be seen that volume 20 fits entirely within form 32.

The value for $\lambda K_{na}$ in this situation is solved from equation (5), and then equations like equations (3) and (4) are applied to produce all the necessary fundamental design data for the appropriate antenna.

It should thus be apparent how, by properly sizing an antenna, like antenna 10, vis-a-vis the subject matter which is to be monitored, time-based changes in dielectric-constant which occur in the monitored regions are readable to produce extremely useful data. In an example like the first one given herein, such data is usable to indicate relative volume changes occurring in the monitored space, and these, in turn, can be interpreted to give other well-known useful information. In the second kind of application, where the monitored space is substantially homogeneous, time-based changes in pressure, and also in temperature, are readily monitored to yield accurate information about other related conditions occurring in the monitored space.

In sizing an antenna to monitor volume changes in something like the heart, and in situations where the to-be-monitored object is deeply embedded, antenna design may have to be based upon ensuring an adequately deep (axially long) defined radiation volume. The heart, of course, is quite close to the outside chest surface; and so, designing to ensure that the maximum diameter of the defined radiation volume encompasses the heart in its large-volume condition is entirely adequate.

While preferred manners of practicing the invention have been described herein, variations are, of course, possible within the scope of the invention.

It is claimed and desired to secure by Letters Patent:

1. A method for monitoring time-based changes in the apparent nominal dielectric constant which characterizes a defined space utilizing a bidirectionally radiating electromagnetic device which has a known radiation axis, and which is energizable to produce, along such axis, a pair of symmetrically axially spaced, defined-power-characteristic radiation volumes, said method comprising:

positioning the device so as to place one of such volumes in a condition substantially completely and congruently embracing such a defined space, and other volume in a condition substantially completely within a body of material having a nominal dielectric constant which is substantially the same as such apparent nominal dielectric constant; and with the device energized, monitoring in such a body of material over time electromagnetic radiation changes that occur in such other volume thereby to determine apparent nominal dielectric constant changes then taking place in the defined space.

2. The method of claim 1 which is employed with a defined space of the kind that includes one volume fraction formed by one medium having one known dielectric constant, surrounded by another volume fraction formed by another medium having a different known dielectric constant, and which further includes the step of interpreting such indicated apparent nominal dielectric constant changes thereby to determine the relative volume changes occurring between such one and other volume fractions.

3. The method of claim 1 which is employed with a defined space of the kind that comprises a single, substantially homogeneous medium having, throughout, such apparent nominal dielectric constant, and which further includes the step of interpreting such indicated apparent nominal dielectric constant changes thereby to determine pressure changes occurring in such medium.

4. The method of claim 1 which is employed with a defined space of the kind that comprises a single, substantially homogeneous medium having, throughout, such apparent nominal dielectric constant, and which further includes the step of interpreting such indicated apparent nominal dielectric constant changes thereby to determine temperature changes occurring in such medium.

* * * * *